United States Patent [19]

Rodriguez et al.

[11] 4,137,236
[45] Jan. 30, 1979

[54] AMINO-SPIRO[OXA(OR THIA)CYCLOALKANE-PENAM]-CARBOXYLIC

[75] Inventors: Ludovic Rodriguez, Brussels; Jacques Leclerca, Braine L'Alleud; Pierre Ykman, Brussels; Eric Cossement, Brussels, all of Belgium

[73] Assignee: U C B, Société Anonyme, Brussels, Belgium

[21] Appl. No.: 869,859

[22] Filed: Jan. 16, 1978

[30] Foreign Application Priority Data

Jan. 18, 1977 [GB] United Kingdom ............... 1905/77

[51] Int. Cl.$^2$ ........................................... C07D 277/04
[52] U.S. Cl. ........................ 260/306.7 C; 260/239.1; 424/271
[58] Field of Search ............................... 260/306.7 C

[56] References Cited

U.S. PATENT DOCUMENTS

| | | | |
|---|---|---|---|
| 3,047,467 | 7/1962 | Doyle et al. | 260/239.1 |
| 3,129,217 | 4/1964 | Doyle et al. | 260/239.1 |
| 3,134,767 | 5/1964 | Doyle et al. | 260/239.1 |
| 3,210,337 | 10/1965 | Chow et al. | 260/239.1 |

Primary Examiner—Nicholas S. Rizzo
Attorney, Agent, or Firm—Wenderoth, Lind & Ponack

[57] ABSTRACT

Amino-spiro[oxa(or thia)cycloalkane-penam]-carboxylic acid, a salt or an ester thereof, of the formula

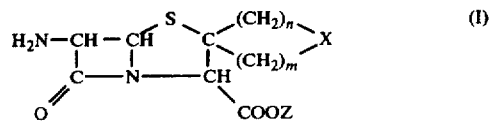

wherein Z is a hydrogen or an alkali metal atom, or a group protecting the carboxylic function, X is a sulfur or oxygen atom, n is 1 or 2, m is 1 or 2, and process of preparing the same.

These compounds are useful as intermediates in the synthesis of a new group of antibiotics having properties similar to penicillins, besides own antibiotic activity with a broad antibacterial spectrum.

6 Claims, No Drawings

AMINO-SPIRO[OXA(OR THIA)CYCLOALKANE-PENAM]-CARBOXYLIC

The present invention relates to new compounds, namely amino-spiro[oxa(or thia)cycloalkane-penam]-carboxylic acids and the salts and esters thereof, as well as to a process of preparing the same and to the use thereof.

These amino-spiro[oxa(or thia)cycloalkane-penam]-carboxylic acids are compounds analogous to the 6-amino-penicillanic acids, wherein the carbon atom in the 2-position of the "penam" ring (see definition below) is substituted by an oxa- or thia-alkylene chain, which forms with this carbon atom a heterocycle. These compounds consequently have a spiro heterocycle, constituted by the penam ring and by a saturated monocyclic heterocycle having an oxygen or sulfur atom.

These compounds are precursors of new penicillins, which are the subject matter of our application No. 869,860 filed concurrently herewith. They also have their own antibiotic activity with a broad antibacterial spectrum, which is by no means negligible as compared with that of the corresponding 6-aminopenicillanic acid.

The new compounds of the present invention have the general formula:

(I)

in which Z is a hydrogen or alkali metal atom or a group protecting the carboxylic function, for example a benzyl group, X is a sulfur or oxygen atom and n and m, which can be the same or different, are 1 or 2, preferably 2.

In view of the existence of three asymmetric carbon atoms at $C_3$, $C_5$ and $C_6$, these compounds (I) can be present in the form of a mixture of 8 isomers which can be grouped into 4 racemic diastereoisomers. The kinetics of the reaction leads, in fact, to the formation of only the 3 alpha, beta and gamma racemates. The alpha racemate, the relative configuration of which corresponds to that of penicillin, is preferably isolated from the reaction mixture.

In the present specification and claims, the nomenclature used is that proposed by R. J. STOODLEY in Progress in Organic Chemistry, 8, (1973), 102–103. In particular, the name "penam" is given to the following ring system:

The compounds of general formula (I) can be prepared by a process, which comprises:

(1) reacting tert-butyl 2-formyl-2-phthalimido-acetate of the formula (II)

with an alpha-amino-mercapto-oxa(or thia)cycloalkaneacetic acid of the formula (III)

wherein X, n and m have the same meanings as above, (2) reacting the resulting alpha-isomer of a tert-butyl alpha-phthalimidodithia(or oxa-thia)-azaspiroalkaneacetate of the formula (IV)

wherein X, n and m have the same meanings as above, with a benzyl halide, (3) subjecting the resulting benzyl ester of the formula (V)

wherein Bz is a benzyl radical and X, n and m have the same meanings as above, to hydrazinolysis, (4) subjecting the resulting tert-butyl alpha-amino-dithia(or oxa-thia)-azaspiroalkaneacetate hydrochloride of the formula (VI)

wherein Bz, X, n and m have the same meanings as above, to partial acid hydrolysis, (5) reacting the resulting alpha-amino-dithia(or oxa-thia)-azaspiroalkaneacetic acid hydrochloride of the formula

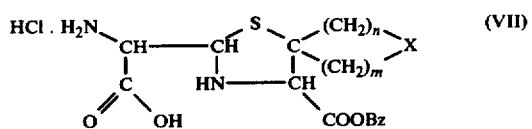 (VII)

wherein Bz, X, n and m have the same meanings as above, with trityl chloride, (6) cyclizing the resulting alpha-tritylamino-dithia(or oxa-thia)-azaspiroalkaneacetic acid of the formula

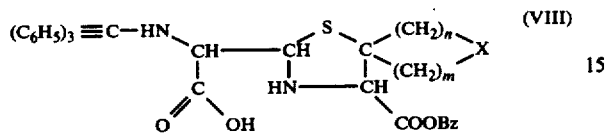 (VIII)

wherein Bz, X, n and m have the same meanings as above, with a carbodiimide, (7) treating the resulting benzyl tritylamino-spiro[oxa(or thia)cycloalkanepenam]-carboxylate of the formula

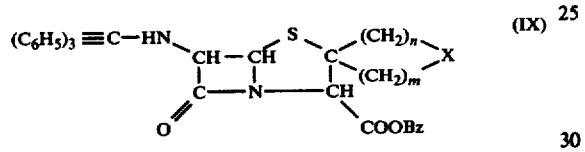 (IX)

wherein Bz, X, n and m have the same meanings as above, with p-toluenesulfonic acid and finally (8) subjecting the resulting benzyl amino-spiro[oxa(or thia)cycloalkanepenam]-carboxylate p-toluenesulfonate of the formula

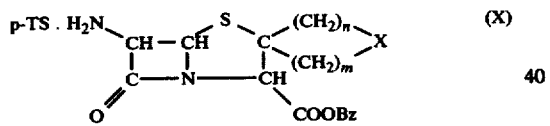 (X)

wherein p-TS represents p-toluenesulfonic acid and Bz, X, n and m have the same meanings as above, to hydrogenolysis to obtain the aminospiro[oxa(or thia)cycloalkane-penam]-carboxylic acid of formula (I), wherein Z is a hydrogen atom.

The preparation of tert-butyl 2-formyl-2-phthalimido-acetate of formula (II) is described in the literature (see Sheehan et al., J.A.C.S., 76, (1954), 158–60).

The starting compounds of formula (III), which are also new, can be prepared, for example, by the following process:

(1) condensing an R' 2-isocyanoacetate of formula (XI) with an oxa(or thia)cycloalkanone of formula (XII), using a suspension of sodium hydride in tetrahydrofuran (THF), to give an R' alpha-formamido-oxa(or thia)cycloalkane-Δ$^\alpha$-acetate of formula (XIII), in accordance with the equation:

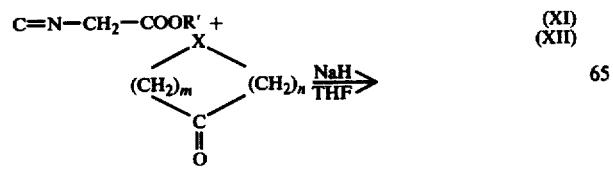

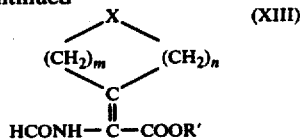 (XIII)

(2) cyclizing (XIII) with phosphorous pentasulfide ($P_4S_{10}$) to give an R' dithia(or oxa-thia)-azaspiroalkene-carboxylate of formula (XIV), in accordance with the equation:

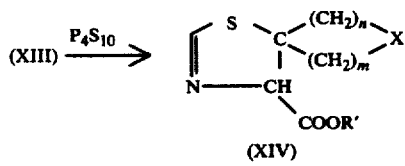

(XIV)

(3) the compound of formula (XIV) is then subjected to hydrolysis, which is accompanied by decyclization, to give an alpha-amino-mercapto-oxa(or thia)-cycloalkaneacetic acid of formula (III), in accordance with the equation:

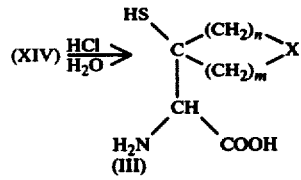

(III)

In these general formulae, R' is an alkyl radical containing 1 to 3 carbon atoms or a benzyl radical, X is an oxygen or sulfur atom, and m and n, which can be the same or different, are 1 or 2.

It is clear that the two enantiomeric forms of the compounds of formula (III) can be separated, which leads directly to the desired diastereoisomer (IV) in a pure form.

USES OF THE COMPOUNDS OF THE PRESENT INVENTION

The interest of the compounds of the present invention resides in the fact that, by simple and known reactions, they give new series of compounds which are analogous to the penicillins. These compounds differ structurally from the known penicillins solely by the presence of the saturated, oxygen- or sulfur-carrying monocyclic heterocycle in the 2-position instead of a gem-dimethyl substituent. These new compounds have the general formula:

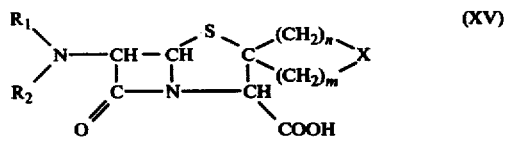 (XV)

in which X is a sulfur or oxygen atom or a sulfinyl group and m and n, which can be the same or different, are 1 or 2.

These compounds as well as processes for preparing the same and uses thereof are the subject matter of our Application Ser. No. 869,860 filed concurrently herewith, to which reference is made for a detailed description.

The substituents $R_1$ and $R_2$ are the conventional substituents known from the chemistry of penicillins, such as those described, for example, in Ullmann's Encyklopadie der Technischen Chemie, 4th Edition, vol. 7, (1974), 651–652.

By way of example, from the compounds of the present invention, there can be obtained acids of general formula (XV), wherein $R_1$ is a hydrogen atom and $R_2$ is a 2-phenylacetyl, 2,6-dimethoxybenzoyl, 2-amino-2-phenylacetyl, 5-methyl-3-phenyl-4-isoxazolecarbonyl or 2-carboxy-2-phenylacetyl radical, or $R_1$ and $R_2$ together represent a divalent organic radical $R_3$, preferably the (hexahydro-1H-azepin-1-yl)methylene radical; as well as the pharmaceutically-acceptable non-toxic salts thereof.

The compounds of formula (XV) in which $R_1$ is a hydrogen atom and $R_2$ is one of the above-mentioned radicals, are obtained by acylating the compounds of the present invention with a halide of a monocarboxylic acid of the formula $R_2$Hal or with a functional equivalent thereof, $R_2$ having the same meaning as above.

For the radicals $R_2$ mentioned above, as acylating agent there can, for example, be used phenylacetyl chloride, 2,6-dimethoxybenzoyl chloride, 5-methyl-3-phenyl-4-isoxazolecarbonyl chloride, 2-phenylglycyl chloride or 2-carboxy-2-phenylacetyl chloride.

As non-limiting examples of functional equivalents of the acid halides mentioned above, which can be used as acylating agents for the primary amino radical of the amino-spiro[oxa(or thia)cycloalkane-penam]-carboxylic acids according to the present invention, there may be mentioned, in particular, acid anhydrides, including mixed anhydrides and especially the mixed anhydrides formed with stronger acids, such as the lower aliphatic monoesters of carbonic acid, the alkylsulfonic and arylsulfonic acids and the acids with a more pronounced hindrance, such as diphenylacetic acid. Furthermore, an azide of an acid or an active ester or thioester (for example with p-nitrophenol, 2,4-dinitrophenol, thiophenol or thioacetic acid) may be used but, as a variant, the free acid itself may be condensed with these amino-spiro[oxa(or thia)cycloalkane-penam]-carboxylic acids, after the free acid has been previously activated by reaction with, for example, (chloromethylene)dimethylammonium chloride (see British Pat. Specification No. 1,008,170 and NOVAK and WEICHET, Experientia, XXI, 6, (1965),360) or by means of enzymes, or with an N,N'-carbonyldiimidazole or an N,N'-carbonylditriazole (see British Pat. Specification No. 967,108), or with a carbodiimide, for example N,N'-dicyclohexylcarbodiimide, N,N'-diisopropylcarbodiimide or N-cyclohexyl-N'-(2-morpholinoethyl)-carbodiimide (see SHEEHAN and HESS, J.A.C.S. 77, (1955),1067) or an alkynylamine (see BUIJLE and VIEHE, Angew. Chem. International Edition, 3, (1964),582), or a keteneimine (see STEVENS and MUNK, J.A.C.S. 80, (1958),4065), or an isoxazolium salt (see WOODWARD et al., J.A.C.S., 83, (1961),1010). Instead of the acid halides, the corresponding azolides can also be used.

When the starting compound used for preparing the compounds of formula (XV) is an amino-spiro[oxa(or thia)cycloalkane-penam]-carboxylic acid of formula (I), in which Z is a group protecting the carboxylic function, preferably a benzyl radical, the synthesis of the compound of formula (XV) comprises a second stage which consists in a hydrogenolysis of the esters obtained to give the corresponding acids.

In this regard, it should be pointed out that the starting compounds for synthesizing the compounds of formula (XV) may be, as desired, the amino-spiro[oxa(or thia)cycloalkane-penam]-carboxylic acids according to the present invention or the salts or esters thereof. However, we have found that it is preferable, with regard to the yield, to use, in certain cases, the esters and, in other cases, the free acids themselves. In particular, when $R_2$ is a 2-phenylacetyl or 2-amino-2-phenylacetyl radical, it is preferable to start from an ester, preferably the benzyl ester, of the corresponding acid, and then to debenzylate the ester so obtained to give the free acid of formula (XV). On the other hand, when $R_2$ is a 5-methyl-3-phenyl-4-isoxazolecarbonyl radical, it is preferable to start from the corresponding free acid. Nevertheless, one must not lose sight of the fact that the amino-spiro[oxa(or thia)cycloalkane-penam]-carboxylic acids are, in all cases, obtained from the corresponding esters, because it is necessary temporarily to protect the acid function during the synthesis. In other words, the conversion of the ester into the acid, which may sometimes be necessary to obtain compounds of formula (XV), is not an additional stage but is merely displaced in the general synthesis. In certain cases, it is carried out before the acylation reaction and in other cases after this acylation reaction.

By "pharmaceutically acceptable non-toxic salts" there are to be understood, in particular, the salts of metals, such as sodium, potassium, calcium and aluminium, the ammonium salts and the amine salts, such as the trialkylamine salts and particularly the salts with triethylamine, procaine, dibenzylamine, N-benzyl-beta-phenethylamine, L-ephenamine, N,N'-dibenzylethylenediamine, dehydroabietylamine, N,N'-bis-dehydroabietyl-ethylenediamine and the N-(lower alkyl)-piperidines, such as N-ethylpiperidine, and, generally speaking, the salts already known for penicillins G and V (see Ullman's Encyklopadie, loc.cit., p.653). The salts may be obtained from the corresponding acids by known methods.

When, in general formula (XV), the radical $R_2$ is, for example, a 2-amino-2-phenylacetyl radical, the compounds may also be in the form of addition salts with pharmaceutically acceptable acids, for example acetic, citric, succinic, ascorbic, hydrochloric, hydrobromic, sulfuric or phosphoric acids.

The compounds of formula (XV), in which $R_1$ and $R_2$ together represent a divalent radical $R_3$, can be obtained from the compounds of the present invention by reaction with an activated derivative of a compound of the formula $R_3=O$, $R_3$ having the same meaning as above. Thus, for example, when the radical $R_3$ is a (hexahydro-1H-azepin-1-yl)methylene radical, the aminospiro[oxa(or thia)cycloalkane-penam]-carboxylic acid or a salt or ester thereof is reacted with an activated derivative of hexahydro-1H-azepine-1-carboxaldehyde. The activated derivatives of the compounds $R_3=O$ are generally the corresponding amide chlorides obtained by reaction with oxalyl chloride, or the complexes obtained by reaction with dimethyl sulfate.

The compounds of formula (XV), as well as their pharmaceutically acceptable non-toxic salts, can be used as antibacterial agents, as dietetic supplements for animal foodstuffs and as therapeutic agents for animals and humans in the treatment of infectious diseases caused by Gram-positive and Gram-negative bacteria.

These compounds possess a very broad spectrum of antibacterial activity, both against Gram-positive and against Gram-negative bacteria but they are most particularly interesting for combating Gram-negative strains which produce beta-lactamases.

PHARMACOLOGICAL PROPERTIES

Numerous comparative tests have been carried out concerning the intrinsic biological activity of the compounds of formula (XV) towards various bacterial strains of the Gram-positive and Gram-negative type. The reference compounds for the comparative tests were penicillin G, oxacillin, ampicillin, methicillin and 6-amino-penicillanic acid. Information is given below regarding the origin and the characteristics of the bacterial strains employed.

A. GRAM-POSITIVE BACTERIAL STRAINS.

STAPHYLOCOCCUS AUREUS 6538

This is a Gram-positive coccus which is particularly sensitive to penicillins and which has a low resistance mechanism. This strain of Staphylococcus is, therefore, representative of a maximum sensitivity of the species.

STAPHYLOCOCCUS AUREUS 52149

This is a Gram-positive coccus, the intrinsic sensitivity of the receptor of which is equivalent to that of the preceding strain but which produces a beta-lactamase which is typical of the species and which renders it resistant to all the penicillins which are sensitive to hydrolysis.

B. GRAM-NEGATIVE BACTERIAL STRAINS.

ESCHERICHIA COLI B.

This is a well-known collection strain of *Escherichia coli* which produces very little beta-lactamase (of type I) and is, therefore, very sensitive to penicillins. As regards the classification of the beta-lactamases, use is here made of that proposed by M. H. RICHMOND and R. B. SYKES (see Advances in Microbial Physiology,9,(1973),pp.43 and 45).

ESCHERICHIA COLI B-AMPI R.

This is a mutant of the preceding strain which we have produced. This strain is, on the other hand, a hyperproducer of beta-lactamase of type I already produced by the parent strain Escherichia coli B. It has an increased resistance to penicillins, which would appear to be directly connected with the production of beta-lactamase.

ESCHERICHIA COLI K 12-44.

This is a mutant of *Escherichia coli* K 12, the typical reference parent strain of the species. This mutant is not a producer of beta-lactamase.

ESCHERICHIA COLI K 12-44 S.

This is a pleiotropic mutant of *Escherichia Coli* K 12-44, which does not produce beta-lactamase and which we have produced. It is very sensitive to penicillins due to hyperpermeability.

ESCHERICHIA COLI K 12-44 R.

This strain is a pleiotropic mutant of *Escherichia coli* K 12-44, which we have produced. It is not a producer of beta-lactamase but, nevertheless, it has a resistance to penicillins, probably as a result of the modification of the permeability of the cell membranes.

C. RESULTS OF THE COMPARATIVE ACTIVITY TESTS.

For a certain number of compounds of formula (XV), the minimum inhibitory concentration (MIC) was determined as follows:

The products to be tested are introduced in increasing concentrations into a gelose culture medium in Petri dishes. A multiple inoculator is used to deposit simultaneously drops (10 microliters) of inoculum (suspension of approximately $10^5$ bacteria per ml) onto the surface of the medium. After incubation at 37° C. for 24 hours, the growth of the bacteria is observed. By definition, the MIC is expressed by the minimum concentration of tested compound which inhibits the multiplication of the bacteia. In the following results, however, the MIC is given as being equal to 1 for the reference compounds and the activity figures given for the tested compounds of formula (XV) are, therefore, relative values. This presentation of the results is more correct and the most reproducible because, for one and the same bacterial strain, different MIC values can be observed if they are measured at different times. This is bound up with the "seasonal" variations in the strains and their nutrient medium.

The compounds which were tested are as follows:

Compound A: 6-(2''-phenylacetamido)-2',3',5',6'-tetrahydro-spiro[penam-2,4'-[4H]pyran]-3-carboxylic acid (potassium salt) (formula XV: $n=m=2$, $X=O$, $R_1=H$, $R_2=2$-phenylacetyl).

Compound B: 6-(2''-amino-2''-phenylacetamido)-2',3',5',6'-tetrahydro-spiro[penam-2,4'-[4H]pyran]-3-carboxylic acid (formula XV: $n=m=2$, $X=O$, $R_1=H$, $R_2=2$-amino-2-phenylacethy);

Compound C: 6-(5''-methyl-3''-phenyl-4''-isoxazolecarboxamido)-2',3',5',6'-tetrahydro-spiro[penam-2,4'-[4H]pyran]-3-carboxylic acid (Na salt) (formula XV: $n=m=2$, $X=O$, $R_1=H$, $R_2=5$-methyl-3-phenyl-4-isoxazolecarbonyl);

Compound D: 6-amino-2',3',5',6'-tetrahydro-spiro[penam-2,4'-[4H]-pyran]-3-carboxylic acid (formula I: $n=m=2$, $X=O$, $Z=H$);

Compound E: 6-(2''-phenylacetamido)-2',3',5',6'-tetrahydro-spiro[penam-2,4'-[4H]thiopyran]-3-carboxylic acid (potassium salt) (formula XV: $n=m=2$, $X=S$, $R_1=H$, $R_2=2$-phenylacetyl);

Compound F: 6-(2''-amino-2''-phenylacetamido)-2',3',5',6'-tetrahydro-spiro[penam-2,4'-[4H]thiopyran]-3-carboxylic acid (formula XV: $n=m=2$, $X=S$, $R_1=H$, $R_2=2$-amino-2-phenylacetyl);

Compound G: 6-(2'',6''-dimethoxybenzamido)-2',3',5',6'-tetrahydro-spiro[penam-2,4'-[4H]thiopyran]-3-carboxylic acid (sodium salt) (formula XV: $n=m=2$, $X=S$, $R_1=H$, $R_2=2,6$-dimethoxybenzoyle);

Compound H: 6-(2''-phenylacetamido)-2',3',5',6'-tetrahydro-spiro[penam-2,4'-[4H]thiopyran]-3-carboxylic acid 1'-oxide (potassium salt) (formula XV: $n=m=2$, $X=SO$, $R_1=H$, $R_2=2$-phenylacetyl);

Compound J: 6-(2''-amino-2''-phenylacetamido)-2',3',5',6'-tetrahydro-spiro[penam-2,4'-[4H]thiopyran]-3-carboxylic acid 1'-oxide (formula XV: $n=m=2$, $X=SO$, $R_1=H$, $R_2=2$-amino-2-phenylacetyl).

a) Comparative tests with penicillin G.

| Strain used | Penicillin G. | Compound A | Compound E | Compound H |
|---|---|---|---|---|
| S.AUREUS 6538 | 1 | 2 | 10 | 1 |
| S.AUREUS 52149 | 1 | 2 | 1 | 1 |
| E.COLI B | 1 | 4 | 5 | 1 |
| E.COLI B AMPI-R | 1 | 2 | >2 | — | b) Comparative tests with oxacillin

| Strain used | Oxacillin | Compound C |
|---|---|---|
| S.AUREUS 6538 | 1 | 2 |
| S.AUREUS 52149 | 1 | 1 | c) Comparative tests with ampicillin.

| Strain used | Ampicillin | Compound B | Compound F | Compound J |
|---|---|---|---|---|
| S.AUREUS 6538 | 1 | | 2 | 2 |
| E.COLI B | 1 | 3.5 | 7 | 1 |
| E.COLI B AMPI-R | 1 | 1 | 3 | 2 |
| E.COLI K 12-44 | 1 | 3.5 | 10 | 3 |
| E.COLI K 12-44S | 1 | 1.9 | 15 | 3 |
| E.COLI K 12-44R | 1 | 1.5 | >1.5 | 2 | d) Comparative tests with 6-amino-penicillanic acid

| Strain used | Penicillanic acid | Compound D |
|---|---|---|
| S.AUREUS 6538 | 1 | 0.5 |
| S.AUREUS 52149 | 1 | 0.5 |
| E.COLI B | 1 | 0.3 |
| E.COLI B AMPI-R | 1 | 0.3 | e) Comparative test with methicillin.

| Strain used | Methicillin | Compound G |
|---|---|---|
| S.AUREUS 52149 | 1 | 0.5 |

It can be seen from these results that the compounds of formula (XV) have activities which are substantially of the same order as those of the corresponding known penicillins. However, the essential interest in these compounds comes forth from the following: the compounds of formula (XV) differ from the known penicillins by an increased resistance to deactivating enzymes, the beta-lactamases, which hydroylze the lactam function of the pencillianic ring.

This propery is demonstrated by the results of the comparison of the hydrolysis kinetics of compound B, with those of ampicillin, in the presence of two beta-lactamases of Gram-negative bacteria. These results are set out in the following Table:

| Residual activities (in micromoles) of ampicillin and compound B in the presence of beta-lactamases, as a function of time |||||||
|---|---|---|---|---|---|---|
| beta-lactamase TEM ||| beta-lactamase P 99 |||
| Incubation time (minutes) | Ampicillin | Compound B | Incubation time (minutes) | Ampicillin | Compound B |
| 0 | 500 | 500 | 0 | 500 | 500 |
| 2 | | 469 | 3 | 262 | 458 |
| 4 | | 453 | 6 | 138 | 422 |
| 6 | <50 | 438 | 9 | <50 | 334 |
| 12 | <50 | 334 | 12 | <50 | 312 |
| 18 | <50 | 225 | 20 | <50 | 300 |

These results show that, after incubation for 6 minutes in beta-lactamase TEM, the activity of ampicillin is no more detectable, whilst there still remains an activity of compound B corresponding to 438 micromoles, i.e. 87%. The same observation was made in the case of beta-lactamase P 99: after incubation for 9 minutes, the activity of ampicillin is no more detectable, whereas there still remains an activity of compound B corresponding to 334 micromoles, i.e. 67%.

These results are also confirmed by the activity tests which have been described above. Indeed, it can be seen that between the activity of compound B on E. COLI B and on its mutant, which is a hyperproducer of beta-lactamase, E. COLI B Ampi-R, there is a difference of a factor of 3.5.

An increased resistance to these beta-lactamases also has been found for compound F. This is however less pronounced than in the case of compound B. No change in behavior towards these beta-lactamases has been detected for compound J, as compared with ampicillin.

A very pronounced increase in resistance to beta-lactamase TEM has also been found for compounds E and H, which are homologues of penicillin G. This property can be shown by measuring the rate of hydrolysis expressed in terms of the number of microliters of sodium hydroxide of a given concentration which are consumed per minute. This method allows the dosage of the penicilloic acid resulting from the hydrolysis of the beta-lactam function by the lytic enzyme. The results of these kinetics, as given in the following Table, clearly show the superiority of compounds E and H as compared with pencillin G.

| Compound | microliters 0.005 N NaOH consumed per minute |
|---|---|
| Penicillin G | 3.83 |
| Compound E | 0.64 |
| Compound H | 0.50 |

This confirms the importance of the compounds of formula (XV) as compared with the known pencillins, particularly for combating the Gram-negative strains which produce beta-lactamases.

D. POSOLOGY AND USE.

The compounds of formula (XV) can be administered orally or parenterally. For example, the posology of compound A is between 0.4 and 6 g per day, that of compound C between 4 and 8 g per day, that of compound E between 2 and 10 g per day and that of compound H between 0.2 and 3 g per day. For the homologues of ampicillin (compounds B, F and J), an identical posology of 0.7 to 7 g per day can be adopted; these doses can of course be adapted in function of the patient and the disease to be treated.

The homologues of 6-amino-penicillanic acid, for example compound D, are not used therapeutically. Nevertheless, merely by way of indication, the activity spectra of 6-amino-pencillanic acid have been compared with those of compound D. These show that compound D has a better activity than 6-amino-penicillanic acid towards both Gram-positive and Gram-negative bacteria.

I. PREPARATION OF ALPHA-AMINO-MERCAPTO-OXA(OR THIA)CYCLOALKANEACETIC ACIDS OF FORMULA (III)

I. 1.
alpha-Amino-4-mercapto-2,3,5,6-tetrahydro-4H-pyran-4-acetic acid

I. 1.a. Ethyl alpha-formamido-2,3,5,6-tetrahydro-4H-pyran-$\Delta^{4,\alpha}$-acetate (formula XIII: n=m=2, X=0, R'=Et)

A solution of 50 g (0.5 mole) of tetrahydro-4H-pyran-4one (formula XII: n=m=2, X=0) and 56.5 g (0.5 mole) of ethyl 2-isocyanoacetate in 300 ml of anhydrous tetrahydrofuran, is added, under nitrogen and at ambient temperature, to a suspension of 12.5 g (0.5 mole) of sodium hydride in 500 ml of anhydrous tetrahydrofuran. The reaction mixture is stirred at ambient temperature for 3 hours. The solvent is evaporated in vacuo and the residue is taken up in a solution of 45 g of acetic acid in 500 ml of water. This solution is extracted with diethyl ether and then the organic phase is washed successively with a 5% aqueous solution of sodium hydrogen carbonate and with water. After drying over anhydrous sodium sulfate, the diethyl ether is evaporated to give 160g of a crude residue which, after recrystallization from a mixture of ethyl acetate and hexane, gives 58 g (yield 55% of theory) of ethyl alpha-formamido-2,3,5,6-tetrahydro-4H-pyran-$\Delta^{4,\alpha}$-acetate; M.P. 109° C.

Analysis for $C_{10}H_{15}NO_4$ (M.W. =213) (as %) calculated: C 56.33; H 7.04; N 6.57. found: 56.20; 7.10; 6.60.

I.1.b. Ethyl 8-oxa-1-thia-3-azaspiro[4,5]-dec-2-ene-4-carboxylate (formula XIV: n=m=2, X=0, R'=Et)

53 g (0.25 mole) of ethyl alpha-formamido-2,3,5,6-tetrahydro-4H-pyran-$\Delta^{4,\alpha}$-acetate and 14.5 g of phosphorous pentasulfide ($P_4S_{10}$) are suspended in 300 ml of anhydrous benzene. After boiling under reflux for 4 hours with stirring, the benzene solution is decanted off from insoluble material, treated with active carbon and filtered over "Hyflo-cel". After evaporating off the solvent, a brownish oil remains behind which distils at 130–135° C/0.5 mm Hg. In this way, there are obtained 30 g (yield 52% of theory) of ethyl 8-oxa-1-thia-3-azaspiro[4,5]-dec-2-ene-4carboxylate which is used without further purification for the continuation of the synthesis. I.1.c. alpha-Amino-4-mercapto-2,3,5,6-tetrahydro-4H-pyran-4acetic acid (formula III: n=m=2, X=0) 2 g (0.0087 mole) of ethyl 8-oxa-1-thia-3-azaspiro[4.5]-dec-2-ene-4-carboxylate are dissolved in 100 ml of 6N hydrochloric acid. The reaction mixture is refluxed for 3 hours and is then concentrated in vacuo in a rotary evaporator. The gummy residue obtained is triturated 3 times with 50 ml of benzene, which are evaporated off under reduced pressure in order to eliminate remaining traces of water and hydrochloric acid. The residue is taken up in 100 ml of water and the solution is treated with "Norite" and then lyophilized. Trituration of the lyophilisate with dry diethyl ether gives 1.6 g of alpha-amino-4-mercapto-2,3,5,6-tetrahydro-4 H-pyran-4-acetic acid hydrochloride (yield: 80.5% of theory). The product gives a single spot in thin layer chromatography on silica (eluent: butanol, acetic acid, water: 4:1:1, Rf:0.35); M.P. 196–197° C (decomposition).

I. 2.
alpha-Amino-4mercapto-2,3,5,6-tetrahydro-4H-thiopyran-4-acetic acid

I. 2.a. Ethyl alpha-formamido-2,3,5,6-tetrahydro-4H-thiopyran-$\Delta^{4,\alpha}$-acetate (formula XIII: n=m32 2, X=S, R'=Et).

A mixture of 127.2 g (1.1 mole) of tetrahydro-4H-thiopyran-4one and 124g (1.1 mole) of ethyl 2-isocyanoacetate in 800 ml of dry tetrahydrofuran is added, accomplished by vigorous agitation and under an atomsphere of dry nitrogen, to a suspension of 29 g of sodium hydride (1.21 mole) in 1.4 liters of anhydrous tetrahydrofuran. Hydrogen is evolved, accompanied by a slight rise in temperature (about 35–40° C). Stirring is maintained overnight and then the solvent is evaporated off in a rotary evaporator in vacuo (at about 25° C). The residue is then carefully treated (exothermal reaction) with a solution of 99 g (1.65 mole) of acetic acid in 1.4 liter of water. The aqueous phase is extracted with chloroform and the organic phase is then washed in turn with a 5% aqueous solution of sodium hydrogen carbonate and with water. After drying over anhydrous sodium sulfate, the chloroform is eliminated in vacuo to leave 210 g of a crude residue. After recrystallization from benzene and chromatography of the mother liquors over silica, there are obtained 173 g of ethyl alpha-formamido-2,3,5,6-tetrahydro-4H-thiopyran-$\Delta^{4,\alpha}$-acetate melting at 112 to 113° C. Yield: 67% of theory.

I.2.b. Ethyl 1,8-dithia-3-azaspiro[4.5]-dec-2-ene-4-carboxylate.

(formula XIV: n=m=2, X=S, R'=Et)

57.2 g (0.25 mole) of ethyl alpha-formamido-2,3,5,6-tetrahydro-4H-thiopyran-$\Delta^{4,\alpha}$-acetate and 15 g (0.0675 mole) of phosphorus pentasulfide ($P_4S_{10}$) are suspended in 600 ml of anhydrous benzene. After heating under reflux for 4 hours with stirring, the benzene solution is decanted off from insoluble material and evaporated to dryness to give 55 g of a residue. This residue is distilled at a pressure of $5.10^2$ mm Hg. Between 154 and 162° C, 27.2 g of ethyl 1,8-dithia-3-azaspiro[4.5]-dec-2-ene-4-carboxylate are obtained (yield 45% of theory). The product is used as it is for the further synthesis.

I.2.c.
alpha-Amino-4-mercapto-2,3,5,6-tetrahydro-4H-thiopyran-4-acetic acid (formula III: n=m=2, X=S)

27.2 g (0.11 mole) of ethyl 1,8-dithia-3-azaspiro[4.5]-dec-2-ene-4-carboxylate are dissolved in 865 ml of 6N hydrochloric acid and boiled under reflux for 5 hours.

The reaction mixture is then concentrated in vacuo in a rotary evaporator. The residue is taken up several times in dry benzene to eliminate traces of water and is then triturated in diethyl ether and filtered. There are obtained 27 g (approx. 100% of theory) of alpha-amino-4-mercapto-2,3,5,6-tetrahydro-4H-thiopyran-4-acetic acid hydrochloride. The product gives a straight spot by thin layer chromatography on silica (eluent: butanol, acetic acid, water: 4:1:1; Rf=0.45); M.P. 193 –197° C.

The following compounds are prepared in the same way:

I.3. alpha-Amino-3-mercapto-tetrahydro-3-furanacetic acid (formula III: n=1, m=2, X=0)

I.4. alpha-Amino-3-mercapto-tetrahydro-3-thiophenacetic acid (formula III: n=1, n=2, X=S)

I.5. alpha-Amino-3-mercapto-3-oxetaneacetic acid (formula III: n=m=1, X=0)

I.6. alpha-Amino-3-mercapto-3-thietaneacetic acid (formula III: n=m=1, X=S)

II. Preparation of tert-butyl alpha-phthalimido-dithia(or oxa-thia)-azaspiroalkane acetates of formula (IV) and of the corresponding benzyl esters of formula (V)

II.1.a. tert-Butyl 4-carboxy-alpha-phthalimido-8-oxa-1-thia-3-azaspiro[4.5]-decane-2-acetate (formula IV: n=m=2, X=0)

28.9 g (0.1 mole) of tert-butyl 2-formyl-2-phthalimido-acetate, 22.75 g (0.1 mole) of alpha-amino-4-mercapto-2,3,5,6-tetrahydro-4H-pyran-4-acetic acid hydrochloride, 12.3 g of sodium acetate, 430 ml of ethanol and 350 ml of water are mixed in a flask at ambient temperature. The reaction mixture is stirred under an atmosphere of nitrogen and gradually heated until it is completely dissolved (65–70° C). Stirring is maintained, whilst gradually allowing the reaction mixture to return to ambient temperature. The reaction mixture is left to stand overnight and then the white precipitate formed (44 g) is filtered off. This product contains a mixture of the alpha, beta and gamma diastereoisomers.

The alpha isomer, which is the only one which is compatible with the stereochemistry of natural penicillin, can be isolated by crystallization of the mixture from pyridine. The epimerization up to thermodynamic equilibrium of the mother liquors is pyridine at 100° C. enriches these in alpha isomer, which may again be separated therefrom by crystallization. The same process is repeated until the alpha isomer can no longer be isolated by crystallization. In this way, 21.5 g of the alpha isomer of tert-butyl 4-carboxy-alphaphthalimido-8-oxa-1-thia-3-azaspiro[4.5]decane-2-acetate are obtained; yield 46.6% of theory; M.P. 199–200° C. (decmposition). Analysis for $C_{22}H_{26}N_2O_7S$ (M.W. =462) (as %) calculated: C 57.14; H 6.63; N 6.06 found: 57.10; 5.70; 6.10.

II.1. b. tert-Butyl 4-benzyloxycarbonyl-alpha-phthalido-8-oxa-1-thia-3-azaspiro[4.5]decane-2-acetate (formula V: n=m=2, X=0).

3.3 g (0.019 mole) of benzyl bromide are added all at once to a solution of 4.62 g (0.01 mole) of the alpha isomer of tert-butyl 4-carboxy-alphaphthalimido-8-oxa-1-thia-3-azaspiro[4.5]decane-2-acetate in 50 ml of dimethylformamide, and then, over a period of 20 minutes, 1.32 g (0.013 mole) of triethylamine in 5 ml of dimethylformamide are added. The reaction mixture is gently stirred overnight at ambient temperature. The clear solution thus obtained is poured into a mixture of ice and water and then extracted with benzene. After washing the organic phase with a 5% aqueous solution of sodium hydrogen carbonate and then with water, it is evaporated to dryness. The residue obtained is recrystallized from diethyl ether to give 4.7 g (0.00085 mole) of tert-butyl 4-benzyloxycarbonyl-alpha-phthalimido-8-oxa-1-thia-3-azaspiro[4.5]decane-2-acetate (yield: 85.2% of theory); M.P. 168–169° C. Another synthesis with quantities 10 times larger gave a yield of 93.6% of theory.

Analysis for $C_{29}H_{32}N_2O_7S$ (M.W.=522) (as %) calculated: C 63.04; H 5.79; N 5.07. found: 63.05; 5.80; 5.03.

II.2.a. tert-Butyl 4-carboxy-alpha-phthalimido-1,8-dithia-3-azaspiro[4.5]-decane-2-acetate (formula IV: n=m=2, X=S).

A solution of 75.7 g (0.924 mole) of sodium acetate in 2.11 liters of water is added all at once and at ambient temperature to a mixture of 178 g (0.616 mole) of tert-butyl 2-formyl-2-phthalimido-acetate and 150 g (0.616 mole) of alpha-amino-4-mercapto-2,3,5,6-tetrahydro-4H-thiopyran-4-acetic acid hydrochloride in 2.11 liters of ethanol.

The reaction mixture is heated to 55 to 60° C. to complete solution (about 5 minutes). The reaction mixture is allowed to return to ambient temperature and stirring is maintained overnight. The precipitate formed (185 g) is filtered off and the mother liquors are concentrated until evaporation of the ethanol is complete, followed by extraction of the residue with chloroform. The extract is dried over anhydrous sodium sulfate and then evaporated in vacuo to give 200 g of residue. The precipitate and the residue, which contain a mixture of the alpha, beta and gamma diastereoisomers are combined and epimerized to give the alpha isomer, which is the only one compatible with the stereochemistry of natural penicillin. The process is the same as that described in paragraph II.1.a. above. In this way, there are obtained 159.6 g of the alpha isomer of tert-butyl 4-carboxy-alpha-phthalimido-1,8-dithia-3-azaspiro[4.5]decane-2-acetate; M.P. 210–212° C.

Analysis for $C_{22}H_{26}N_2O_6S_2$ (M.W.=478) (as %) calculated: C 55.2; H, 5.44; N 5.85. found: 56.1; 5.50; 5.80.

II.2.b. tert-Butyl 4-benzyloxycarbonyl-alpha-phthalimido-1,8-dithia-3-azaspiro[4.5]decane-2-acetate (formula V: n=M=2, X=S) 1.34 g (0.013 mole) of triethylamine are added dropwise, whilst maintaining the temperature at about 25° C. with an ice bath to a solution of 3.26 g (0.019 mole) benzyl bromide and 4.8 g (0.01 mole) of the alpha isomer of tert-butyl 4-carboxy-alpha-phthalimido-1,8-dithia-3-azaspiro[4.5]-decane-2-acetate in 50 ml of dimethylformamide.

Stirring is maintained overnight at ambient temperature. The clear solution thus obtained is poured on to a mixture of ice and water and extracted with benzene. The benzene phase is separated and the washed successively with 5% aqueous sodium hydrogen carbonate solution and water. It is dried and evaporated to dryness and the crude product obtained is recrystallized from a mixture of benzene and hexane. tert-Butyl 4-benzyloxycarbonyl-alphaphthalimido-1,8-dithia-3-azaspiro[4.5]- decane-2-acetate thus obtained (4.2 g; 75% of theory) melts at 197–198° C.

Analysis for $C_{29}H_{32}N_2O_6S_2$ (M.W. =568) (as %) calculated: C 61.3; H 5.64; N 4.93. found: 62.0; 5.62; 4.88.

The following compounds are prepared in the same way:

II.3. a. tert-Butyl 4-carboxy-alpha-phthalimido-7-oxa-1-thia-3-azaspiro[4.4]nonane-2-acetate (formula IV: n=1, m=2, X=O).

II.3.b. tert-Butyl 4-benzyloxycarbonyl-alpha-phthalimido-7-oxa-1-thia-3-azaspiro[4.4 nonane-2-acetate (formula V: n=1, m=2, X=O).

II.Lb 4.a. tert-Butyl 4-carboxy-alpha-phthalimido-1,7-dithia-3-azaspiro[4.4]nonane-2-acetate (formula IV: n=1, m=2, X=S).

II.4.b. tert-Butyl 4-benzyloxycarbonyl-alpha-phthalimido-1,7-dithia-3-azaspiro[4.4 nonane-2-acetate (formula V: n=1, m=2, X=S).

II.5.a. tert-Butyl 8-carboxy-alpha-phthalimido-2-oxa-5-thia-7-azaspiro[3.4]octane-6-acetate (formula IV- n=m=1, X=O).

II.5.b tert-Butyl 8-benzyloxycarbonyl-alpha-phthalimido-2-oxa-5-thia-7-azaspiro[3.4]octane-6-acetate (formula V: n=m=1, X=O).

II.6a. tert-Butyl 8-carboxy-alpha-phthalimido-2,5-dithia-7-azaspiro[3,4]-octane-6-acetate (formula IV* n=m=1, X=S).

II.6.b. tert-Butyl 8-benzyloxycarbonyl-alpha-phthalimido-2,5-dithia-7-azaspiro[3.4]octane-6-acetate (formula V: n=m=1, X=S).

III. Preparation of tert-butyl alpha-amino-dithia(or oxa-this)-azaspiroalkane-acetates of formula (VI) and of the corresponding alpha-amino-dithia(or oxa-this)-azaspiroalkaneacetic acids of formula (VIII)

III.1.a. tert-Butyl alpha-amino-4-benzyloxycarbonyl-8-oxa-1-thia-3-azaspiro-[4.5]decane-2-acetate (formula VI: n=m=2, X=O)

4.4 ml of a solution of anhydrous dimethylformamide containing 2 moles per liter of hydrazine hydrate (0.0088 mole) are added dropwise at 0° C. under an atmosphere of nitrogen to a suspension of 4.4 g (0.008 mole) of tert-butyl 4-benztloxycarbonyl-alpha-phthalimido-8-oxa-1-thia-3-azaspiro[4.5]decane-2-acetate in 6 ml of anhydrous dimethylformamide. The reaction mmixture is allowed to return gradually to ambient temperature (within about 30 minutes). To the light yellow solution thus obtained are added dropwise 7.7 ml of 1.18N hydrochloric acid. The reaction medium becomes turbid and then crystallizes in bulk. After one hour, the precipitate is filtered off, redissolved in chloroform containing a little methanol, filtered, dried and evaporated to dryness. The residue obtained is restriturated with hexane to give 3.3 g (0.0072 mole) of tert-butyl alpha-amino-4-benzyloxycarbonyl-8-oxa-1-thia-3-azaspiro[4.5]decane-2-acetate hydrochloride (yield 90% of theory); M.P. 156–157° C.

III.1b. alpha-Amino-4-benzyloxycarbonyl-8-oxo-1-thia-3-azaspiro[4.5decane-2-acetic acid (formula VII: n=m=2, X=O).

Dry gaseous hydrogen chloride is bubbled into a suspension of 6.6 g (0.0144 mole) of tert-butyl alpha-amino-4-benzyloxycarbonyl-8-oxa-1-thia-3-azaspiro[4,5]decane-2-acetate hydrochloride in 150 ml of anhydrous nitromethane at 0° C. After 15 minutes, most of the product has dissolved and the bubbling of hydrogen chloride is continued for 1 hour. Insoluble material is filtered off and the nitromethane solution is degassed at a pressure of 20 mm Hg in a rotary evaporator at ambient temperature to eliminate as much gaseous hydrogen chloride as possible. 700 ml of anhydrous diethyl ether are added, followed by cooling to -5° C. for 4 hours. In this way, a precipitate is obtained which is filtered off, washed with diethyl ether and dried in vacuo to give 4.2 g (0.0104 mole) of alpha-amino-4-benzyloxycarbonyl-8-oxa-1-thia-3-azaspiro[4.5]decane-2-acetic acid hydrochloride (yield: 72.5% of theory); M.P. 152–153° C.

III.2.a. tert-Butyl alpha-amino-4-benzyloxycarbonyl-1,8-dithia-3-azaspiro[4.5]-decane-2-acetate (formula VI: n=m=2, X=S)

151.5 ml of a solution of dimethylforamide containing 2 moles per liter of hydrazine hydrate (0.3025 mole) are added, between 0 and 5° C., to a suspension of 156.3 g (0.275 mole) of tert-butyl 4-benzyloxycarbonyl-alpha-phthalimido-1,8-dithia-3-azaspiro[4.5]decane-2-acetate in 170 ml of anhydrous dimethylformamide. The addition is carried out over 75 minutes and is accompanied by a complete dissolution of the product. The reaction mixture is allowed to return to ambient temperature over a period of 1 hour, whereafter 309 ml of 1N hydrochloric acid are added dropwise at 20 to 25° C. The precipitate of phthaloghydrazide formed is filtered off and the mother liquors are evaporated to dryness. The residue is taken up in methanol and is precipitated with diethyl ether. In this way, there are obtained 119.1 g of tert-butyl alpha-amino-4-benzyloxycarbonyl-1,8-dithia-3-azaspiro[4.5]decane-2-acetate hydrochloride (yield 91.5% of theory); M.P. 178–181° C.

Analysis for $C_{21}H_{30}N_2O_4S_2.HCl$ (M.W.=475) (as %) calculated : C 53.00; H 6.53; H 5.90. found : 52.98; 6.54; 5.85.

III.2b. alpha-Amino-4-benzyloxycarbonyl-1,8-dithia-3-azaspiro[4.5]decane-2-acetic acid (formula VII: n=m=2, X=S).

Dry gaseous hydrogen chloride is bubbled into a suspension of 39.1 g (0.0824 mole) of tert-butyl alpha-amino-4-benzyloxycarbonyl-1,8-diethia-3-azaspiro[4.5]-decane-2-acetate hydrochloride in 1.3 liter of anhydrous nitromethane, at a temperature between 0 and -5° C. over a period of 90 minutes. After filtration, there are obtained 27.7 g of alpha-amino-4-benzyloxycarbonyl-1,8-dithia-3-azaspiro[4.5]decane-2-acetic acid hydrochloride (yield approx. 80% of theory); M.P. 170–173° C. (decomposition).

The following compounds are prepared in the same way:

III.3.a. tert-Butyl alpha-amino-4-benzyloxycarbonyl-7-oxa-1-thia-3-azaspiro-[4.4]nonane-2-acetate (formula VI: n=1, m=2, X=O)

III.3.b. alpha-Amino-4-benzyloxycarbonyl-7-oxa-1-thia-3-azaspiro[4,4]nonane-2-acetic acid (formual VII: n=1, m=2, X=O).

III.4.a. tert-Butyl alpha-amino-4-benzyloxycarbonyl-1,7-dithia-3-azaspiro-[4.4]nonane-2-acetate (formula VI: n=1, m=2, X=S).

III.4.b. alpha-Amino-4-benzyloxycarbonyl-1,7-dithia-3-azaspiro[4,4]nonane-2-acetic acid (formula VII: n=1, m=2, X=S).

III.5.a. tert-Butuyl alpha-amino-8-benzyloxycarbonyl-2-oxa-5-thia-7-azaspiro-[3.4]octane-6-acetate (formula VI: n=m=1, X=O).

III.5.b. alpha-Amino-8-benzyloxycarbonyl-2-oxa-5-this-7-azas-piro[3.4]octane-6-acid (formula VII: n=m=1, X=O).

III.6.a. tert-Butyl alpha-amino-8-benzyloxycarbonyl-2,5-dithia-7-azaspiro[3.4]-octane-6-acetate (formula VI: n=m=1, X=S).

III.6.b. alpha-Amino-8-benzyloxycarbony-2,5-dithia-7-azaspiro[3.4]octane-6-acetic acid (formula VII: n=m=1, X=S).

IV. Preparation of benzyl 6-tritylammino-spriro[oxa(or this)cycloalkane-penam]-carboxylates of formula (IX)

IV.1.Benzyl 6-tritylamino-2',3',5',6'-tetrahydro-spiro[penam-2,4'[4H]pyran]-3-carboxylate (formula IX: n=m=2, X=O).

43 g (0.107 mole) of alpha-amino-b 4-benzyloxcarbonyl-8-oxa-1-thia-3-azaspiro[4.5]decane-2-acetate acid hydrochloride and 100 g (0.36 mole) of trityl chloride are mixed in 750 ml of anhydrous dichloromethane. The reaction mixture is cooled to -20° C. Over a period of 90 minutes, there are added 100 g (1 mmole) of triethylamine in 200 ml of anhydrous dichloromethane. The reaction mixture is left to stand overnight at -5° C. and is then poured onto a mixture of ice and water which is acidified to pH 6 be means of dilute phosphoric acid. The aqueous phase is extracted with chloroform annd the chloroform extract is then washed with water. After drying and evaporation, there are obtained 160 g of an amorphous product which is redissolved in 800 ml of dry nitromethane. 55 g (0.437 mole) of N,N'-diisopropylcarbodiimide (DCI) in 100 ml of dichloromethane are added to this solution. A precipitate of N,N'-diisopropylurea appears gradually and the reaction is allowed to continue overnight. The precipitate is filtered off and the solvent evaporated off in vacuo to give 147 g of solid product. A first crystallization from a mixture of benzene-hexane, followed by a second from a mixture of diethyl ether and hexane, finally gives 46.5 g of benzyl 6-trithylamino-2',3',5',6'-tetrahydro-sprio[penam-2,4'[4H)pyran]-3-carboxylate (yield 73.6% of theory); M.P. 144–145° C.

Analysis for $C_{36}H_{34}N_2O_4S$ (M.W.=590) (aS %) calculated : C 73.22; H 5.76; N 4.74. found : 73.30; 6.01; 4.80.

IV.2. Benzyl 6-tritylamino2', 3',5'6',5'-tetrahydro-spiro[penam-2,4'-[4H]thiopyran]-3-carboxylate (formula IX: n=m=2, X=S).

3.42 g (0.012 mole) of trityl chloride are added all at once at -10° C. to a suspension of 1.4 g (0.0033 mole) of alpha-amino-4-benzyloxycarbonyl-1,8-dithia-3-azaspiro[4.5]decane-2-acetic acid hydrochloride in 30 ml of anhydrous dichloromethane, followed by the dropwise addition of a solution of 3.25 g (0.0322 mole) of triethylamine in 30 ml of dichloromethane. After leaving the reaction mixture to stand overnight in a refrigerator, the solution is poured on to 100 ml of a mixture of ice and water, followed by acidification to pH 6 with phosphoric acid. The organic phase is decanted off, washed with water, dried over anhydrous sodium sulfate and evaporated to give 4.7 g of a crude residue. This residue is taken up in 30 ml of nitromethane, followed by adding at ambient temperature 1.68 g (0.0134 mole) of DCI. The reaction mixture is stirred overnight, insoluble material is filtered off, the filtrate is evaporated to dryness and the residue is chromatographed over silica. There is obtained 0.8 g benzyl 6-tritylamino-2',3',5',6'-tetrahydro-spiro[penam-2,4'-[4H]thiopyran]-3-carboxylate which, after recrystallization from a mixture of ddiethyl ether and hexane, melts at 147–148° C.

Analysis for $C_{36}H_{34}N_2O_3S_2$ (M.W. =606) (as &) calculated : C 71.25 H 5.61 N 4.62 found : 71.18 5.62 4.59

The following compounds are prepared in the same way:

IV.3. Benzyl 6'-tritylamino-4,5-dihydro-spriro[furan-3(2H), 2'-penam]-3-carboxylate (formula IX: n=1, m=2, X=O).

IV.4. Benzyl 6-tritylamino-4',5'-dihydro-spiro]penam-2,3'(2'H)-thiophene]-3-carboxylate (formula IX: n=1, m=2, X=S).

IV.5. Benzyl 6'-trithylamino-spiro]oxetane-3,2'-penam]-3-carboxylate (formula IX: n=m=1, X=O).

IV.6. Benzyl 6-tritylamino-spiro]penam-2,3'-thiethane]-3-carboxylate (formula IX: n=m=1, X=S).

V. Preparation of benzyl amino-spiro[oxa(or thia)cycloalkane-penam]-carboxylate p-toluenesulfonates of formula (X).

V.I. Benzyl 6-amino-2',3',5',6'-tetrahydro-spiro[penam-2,4'-[4H]pyran]-3-carboxylate p-toluenesulfonate (formula X: n=m=2, X=O).

5.7 g (0.3 mole) of p-toluenesulfonic acid monohydrate are added all at once, accompanied by stirring and at ambient temperature to a suspension of 17.7 g (0.03 mole) of benzyl 6-ritylamino-2',3',5',6'-tetrahydro-spiro[penam2,4'[4H]pyran]-3-carboxylate in 100 ml of acetone. After rapid dissolution of the trityl compound, the p-toluenesulfonate precipitate gradually over the course of 3 hours. 300 ml anhydrous diethyl ether are then added, followed by vigorous stirring and filtration. After rinsing the precipitate with diethyl ether and drying it, there are obtained 13.6 g of benzyl 6-amino-2',3', 5',6'-tetrahydro-spiro[penam-2,4'-[4H]pyran]-3- carboxylate p-toluenesulfonate (yield 87.2% of theory); M.P. 163–164° C.

Analysis for $C_{17}H_{20}N_2O_4S\text{-}C_7H_8O_3S$ (M.W.=520) (as %) calculated : C 55.38; H 5.38; N 5.38. found : 55.45; 5.45; 5.36.

V.2. Benzyl 6-amino-2',3',5',6'-tetrahydro-spiro[penam-2,4'-[4H]thiopyran]-3-carboxylate p-toluenesulfonate (formula X: n=m=2, X=S)

0.4 g (0.0006 mole) of benzyl 6-tritylamino-2',3',5',6'-tetrahydrospiro[penam-2,4'-[4H]thiopyran]-3-carboxylate are suspended in 3.5 ml of anhydrous acetone. A solution of 0.125 g (0.000 6 mole) of p-toluenesulfonic acid monohydrate in 3.5 ml of anhydrous acetone is added dropwise. A bulk precipitate is produced which is diluted with 8 ml of acetone. After filtering and rinsing with diethyl ether, there is obtained 0.3 g of benzyl 6-amino-2', 3',5',6'-tetrahydro-spiro[pename-2,4'-[4H]thipyran]-3-carboxylate p-toluenesulfonate; M.P. 171–173° C.

Analysis for $C_{17}H_{20}N_2O_3S_2\text{-}C_7H_8O_3S$ (M.W.=536) (as %) calculated : C 53.70; H 5.22; N 5.22; found : 53.568; 5.21; 5.27;

The following compounds are prepared in the same way in the form of their p-toluenesulfonates:

V.3. Benzyl 6'-amino-4,5-dihydro-spiro[furan-3(2H),2'-penam]-3'-carboxylate (formula X: n=1, m=2, X=O)

V.4. Benzyl 6-amino:4',5'-dihydro-spiro[penam-2,3'(2'H)-thiophene]-3carboxylate (formula X: n=1, m=2, X=S)

V.5. Benzyl 6'-amino-spiro[oxetane-3,2'-penam]-3'-carboxylate (formula X: n=m=1, X=O)

V.6. Benzyl 6-amino-spiro[penam-2,3'-thietane]-3-carboxylate (formula X: n=m=1, X=S)

VI. Preparation of amino-spiro[oxa(or thia)cycloakane-penam]-carboxylate acids of formula I

VL.1. 6-amino-2',3',5',6'-tetrahydro-spiro[penam-2,4'-[4H]pyran]-3-carboxylic acid (formula I: n=m=2, X=O, Z=H)

0.660 g (0.006 mole) of triethylamine are added all at once at ambient temperatuure to a suspension of 3.12 g (0.006 mole) of benzyl 6-amino-2',3',5', 6'-tetrahydro-spiro[penam-2,4'-[4H]pyran-3-carboxylate p-toluenesulfonate in 200 ml of dichloromethane. The dichloromethane phase is separated off, washed with water, dried over anhydrous sodium sulfate and evaporated to dryness. In this way, 2.6 g of free base are obtained. This is redissolved in 600 ml of 96% ethanol and is hydrogenolyzed for 16 hours at a pressure of 3 kg hydrogen in the presence of 5 g of Pd/C catalyst containing 10% palladium. The reaction mixture is filtered over 37 Hyflor-cel", the filtrate is evaporated to dryness and the residue is taken up in diethyl ether, filtered and dried. In this way, there is obtained 1.22 g (yield 79% of theory) of 6-amino-2',3',5',6'-tetrahydrospiro[penam-2,4'-[4H]pyran]-3-carboxylic acid; M.P. 189–192° C.

Analysis for $C_{10}H_{14}N_2O_4S$ (M.W.=258) (as %) calculaed: C 46.5; H 5.42; N 10.83. Found : 46.3; 5.89; 9.30.

| Infra-red spectrum (KBr) | |
|---|---|
| cm$^{-1}$ | Attributions |
| 3500–2500 | $NH_3^+$ |
| 2950 | $CH_2$ and CH |
| 1765 | CO beta-lactam |
| 1580 | $COO^-$ |
| 1510 | $NH_3^+$ |

The following compounds are prepared in the same way:

VI.2. 6-amino-2',3',5',6'-tetrahydro-spiro[penam-2,4'-[4H]thiopyran9 -3carboxylic acid (formula I: n=m=2, X=S, Z=H).

Vi.3. 6'-amino-4,5-dihydro-spiro[furan-3(2H),2'-penam]-3'-carboxylic acid (formula I: n=1, m=2, X=O, Z=H).

VI.4. 6-amino:4',-dihydro-spiro[penam-2,3'(2'H)-thiophene]-3-carboxylic acid (formula I: n=1, m=2, X=S, Z=H).

VI.5. 6'-amino-spiro[oxetane-3,2'-penam]-3'-carboxylic acid (formula I: n=m=1, X=O, Z=H).

VI.6. 6-amino-spiro[penam-2,3'-thietane]-3-carboxylic acid (formula I: n=m=1, X=S, Z=H).

We claim:

1. An amino-spiro [oxa(or thia)cycloalkane-penam]-carboxylic acid, a salt of an ester thereof, of the formula

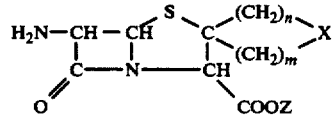

wherein
Z is a hydrogen or an alkali metal atom, or a group protecting the carboxylic function,
X is a sulfur or oxygen atom,
n is 1 or 2,
m is 1 or 2.

2. A compound as claimed in claim 1, wherein Z is a benzyl radical.

3. A compound as claimed in claim 1, namely 6-amino-2',3',5',6'tetrahydro-spiro[penam-2,4'-[4H]pyran]-3-carboxylic acid.

4. A compound as claimed in claim 1, namely benzyl 6-amino-2',3',5', 6'-tetrahydro-spiro[penam-2,4'[4H]pyran9 -3-carboxylate.

5. A compound as claimed in claim 1, namely 6-amino-2',3',5',6'-tetrahydro-spiro[penam-2,4'-[4H]thiopyran]-3-carboxylic acid.

6. A compound as claimed in claim 1, namely benzyl 6-amino-2',3',5',6'tetrahydro-spiro[penam-2,4'-[4H]thiopyran]-3-carboxylate.

* * * * *